US012082961B2

(12) United States Patent
Sun et al.

(10) Patent No.: US 12,082,961 B2
(45) Date of Patent: Sep. 10, 2024

(54) SYSTEM AND METHOD FOR PET IMAGING

(71) Applicant: SHANGHAI UNITED IMAGING HEALTHCARE CO., LTD., Shanghai (CN)

(72) Inventors: Yixing Sun, Shanghai (CN); Kun Wu, Shanghai (CN); Shitao Liu, Shanghai (CN); Shaohui An, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 304 days.

(21) Appl. No.: 17/595,438

(22) PCT Filed: May 17, 2019

(86) PCT No.: PCT/CN2019/087320
§ 371 (c)(1),
(2) Date: Nov. 17, 2021

(87) PCT Pub. No.: WO2020/232563
PCT Pub. Date: Nov. 26, 2020

(65) Prior Publication Data
US 2022/0249046 A1 Aug. 11, 2022

(51) Int. Cl.
*A61B 6/00* (2024.01)
*A61B 6/03* (2006.01)
(Continued)

(52) U.S. Cl.
CPC ........... *A61B 6/4488* (2013.01); *A61B 6/037* (2013.01); *G01T 1/20184* (2020.05); *G01T 1/20188* (2020.05); *G01T 1/2985* (2013.01)

(58) Field of Classification Search
CPC ............. G01T 1/20184; G01T 1/20188; G01T 1/2985; A61B 6/4488; A61B 6/037
See application file for complete search history.

(56) References Cited

U.S. PATENT DOCUMENTS 7,488,949 B2 * 2/2009 Ueno .................. A61B 6/4488
250/370.15
2014/0367577 A1 * 12/2014 Badawi ................ A61B 6/037
250/361 R
(Continued)

FOREIGN PATENT DOCUMENTS

CN 204600511 U 9/2015
CN 105769230 A 7/2016
(Continued)

OTHER PUBLICATIONS

International Search Report in PCT/CN2019/087320 mailed on Feb. 13, 2020, 5 pages.
(Continued)

*Primary Examiner* — David P Porta
*Assistant Examiner* — Casey Bryant
(74) *Attorney, Agent, or Firm* — METIS IP LLC

(57) ABSTRACT

The present disclosure relates to a detector apparatus. The detector apparatus may include a detecting module, an electronics module and a cooling assembly. The detecting module may be configured to detect radiation rays emitted from a subject and generate electrical signals in response to detection of radiation rays. The electronics module may be configured to process the electrical signals generated by the detecting module. The cooling assembly may be configured to cool the detecting module and the electronics module. The cooling assembly may include a first layer and a second layer. The first layer may be thermally connected with the detecting module, and the second layer may be thermally connected with the electronics module.

18 Claims, 8 Drawing Sheets

(51) Int. Cl.
    *G01T 1/20*         (2006.01)
    *G01T 1/29*         (2006.01)

(56)     References Cited

U.S. PATENT DOCUMENTS

| | | | |
|---|---|---|---|
| 2016/0187496 A1* | 6/2016 | Bradford | G01T 1/2985 |
| | | | 250/366 |
| 2018/0356536 A1 | 12/2018 | Glowacz et al. | |
| 2019/0000406 A1* | 1/2019 | Liu | A61B 6/4258 |
| 2020/0037968 A1* | 2/2020 | Takayasu | G01T 1/20182 |
| 2022/0071057 A1* | 3/2022 | Konkle | H05K 7/20136 |

FOREIGN PATENT DOCUMENTS

| | | | |
|---|---|---|---|
| CN | 108186040 A | | 6/2018 |
| CN | 109567842 A | | 4/2019 |
| CN | 208677416 U | | 4/2019 |
| CN | 208837979 U | * | 5/2019 |
| WO | 2017010896 A1 | | 1/2017 |

OTHER PUBLICATIONS

Written Opinion in PCT/CN2019/087320 mailed on Feb. 13, 2020, 6 pages.

* cited by examiner

SYSTEM AND METHOD FOR PET IMAGING

This application is a U.S. national stage under 35 U.S.C. § 371 of International Application No. PCT/CN2019/087320, filed on May 17, 2019, designating the United States of America, the contents of which are hereby incorporated by reference.

TECHNICAL FIELD

The present disclosure generally relates to positron emission tomography (PET), and more specifically, relates to a PET detector assembly.

BACKGROUND

PET is an exemplary nuclear medicine imaging technique used to generate images that may reflect metabolic activities of a specific organ or tissue (e.g., a tumor). A detector assembly used in PET may receive radiation rays (e.g., γ rays) generated from a patient's body indirectly by tracer molecules and provide information relating to the metabolic activities at locations of the tracer molecules, which in turn provides functional information of the patient. A PET detector assembly of a PET imaging system may include a plurality of detecting cells arranged in a substantially cylindrical configuration. In general, each of the plurality of detecting cells may be formed by connecting one or more crystal array together by adhesive, which may be difficult to disassemble and repair the detecting cells. In addition, the PET detector assembly may include a cooling assembly for cooling the plurality of detecting cells. An integrated cooling plate is widely used in the PET detector assembly to cool one of the plurality of modules, which may decrease cooling efficiency. Therefore, it is desirable to provide PET imaging system with improved detector assembly and cooling assembly.

SUMMARY

According to one aspect of the present disclosure, a detector apparatus is provided. The detector apparatus may include a detecting module, an electronics module and a cooling assembly. The detecting module may be configured to detect radiation rays emitted from a subject and generate electrical signals in response to detection of radiation rays. The electronics module may be configured to process the electrical signals generated by the detecting module. The cooling assembly may be configured to cool the detecting module and the electronics module. The cooling assembly may include a first layer and a second layer. The first layer may be thermally connected with the detecting module, and the second layer may be thermally connected with the electronics module.

In some embodiments, the first layer and the second layer may be part of a cooling plate. The first layer and the second layer may be thermally disconnected from each other. The cooling plate may be mounted between the detecting module and the electronics module.

In some embodiments, the first layer may be made of a first cooling plate. The second layer may be made of a second cooling plate. The first cooling plate may be spatially separate from the second cooling plate.

In some embodiments, the first cooling plate and the second cooling plate may be mounted between the detecting module and the electronics module.

In some embodiments, the cooling assembly may further include one or more thermally insulating layers mounted between the first layer and the second layer.

In some embodiments, the first layer may be in fluid communication with the second layer.

In some embodiments, the first layer may include a first flow channel. The second layer may include a second flow channel. The first flow channel and the second flow channel may be configured to accommodate one or more cooling mediums.

In some embodiments, the cooling assembly may further include one or more connectors. The first flow channel may be in fluid communication with the second flow channel via the one or more connectors.

In some embodiments, the cooling assembly may further include an inlet mounted on the first layer, and an outlet mounted on the second layer.

In some embodiments, at least one of the first flow channel or the second flow channel may have a curved shape.

In some embodiments, the second flow channel may have a serpentine shape.

In some embodiments, a temperature gradient of the detector apparatus may be less than a threshold when the detector apparatus is in operation.

In some embodiments, the threshold may be 0.6 degrees Celsius.

In some embodiments, at least a portion of the cooling assembly may be made of aluminum.

In some embodiments, the detecting module may include a plurality of detecting cells. Each of the plurality of detecting cells may include a detecting unit and a first electronics unit. The detecting unit may be configured to generate visible light signals in response to detection of the radiation rays. The first electronics unit may be configured to convert the visible light signals into electrical signals.

In some embodiments, each of the plurality of detecting cells may be detachable.

In some embodiments, a count of the plurality of detecting cells in the detector apparatus may be adjustable.

In some embodiments, the first layer may be connected with the first electronics unit of each of at least a portion of the plurality of detecting cells.

In some embodiments, the electronics module may include one or more second electronics units. The one or more second electronics units may be configured to process the electrical signals generated by the one of the plurality of detecting cells. Each of the one or more second electronics units may be associated with one of the plurality of detecting cells.

In some embodiments, the electronics module may include one or more second electronics units configured to process the electrical signals generated by the at least two of the plurality of detecting cells. Each of the one or more second electronics units may be associated with at least two of the plurality of detecting cells.

According to another aspect of the present disclosure, a detector apparatus of a scanner is provided. The detector apparatus of a scanner may include a detecting module and an electronics module. The detecting module may be configured to detect radiation rays emitted from a subject and generate electrical signals in response to detection of radiation rays. The electronics module may be configured to process the electrical signals generated by the detecting module. The detecting module may include a plurality of detecting cells arranged along at least one of an axial direction or a circumferential direction perpendicular to the axial direction of the scanner. Each of the plurality of detecting cells may include a detecting unit configured to generate visible light signals in response to detection of the radiation rays and an electronics unit configured to convert the visible light signals into the electrical signals. At least one of the plurality of detecting cells may be detachable.

In some embodiments, the detector apparatus may further include a cooling assembly. The cooling assembly may be configured to cool the detecting module and the electronics module. The cooling assembly may include a first layer and a second layer. The first layer may be thermally connected with the detecting module. The second layer may be thermally connected with the electronics module.

According to still another aspect of the present disclosure, an imaging device may be provided. The imaging device may include a gantry and a plurality of detector apparatuses. The gantry may include a detection region to accommodate a subject. The plurality of detector apparatuses may be arranged along a circumferential direction of the gantry. Each of the plurality of detector apparatuses may include a plurality of detecting cells and an electronics module arranged along an axial direction of the gantry that is perpendicular to the circumferential direction. At least some of the plurality of detecting cells may be detachably mounted on the gantry. The plurality of detecting cells may be configured to generate electrical signals in response to detection of radiation rays emitted from the subject. The electronics module may be configured to process the electrical signals generated by the plurality of detecting cells.

In some embodiments, each of the plurality of detector apparatuses may further include a cooling assembly configured to cool the detecting module and the electronics module. The cooling assembly may include a first layer and a second layer. The first layer may be thermally connected with the detecting module. The second layer may be thermally connected with the electronics module.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. The term first, second and the like in the claims and the description of the present disclosure do not mean any sequential order, number or importance, but are only used for distinguishing different components. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 1:
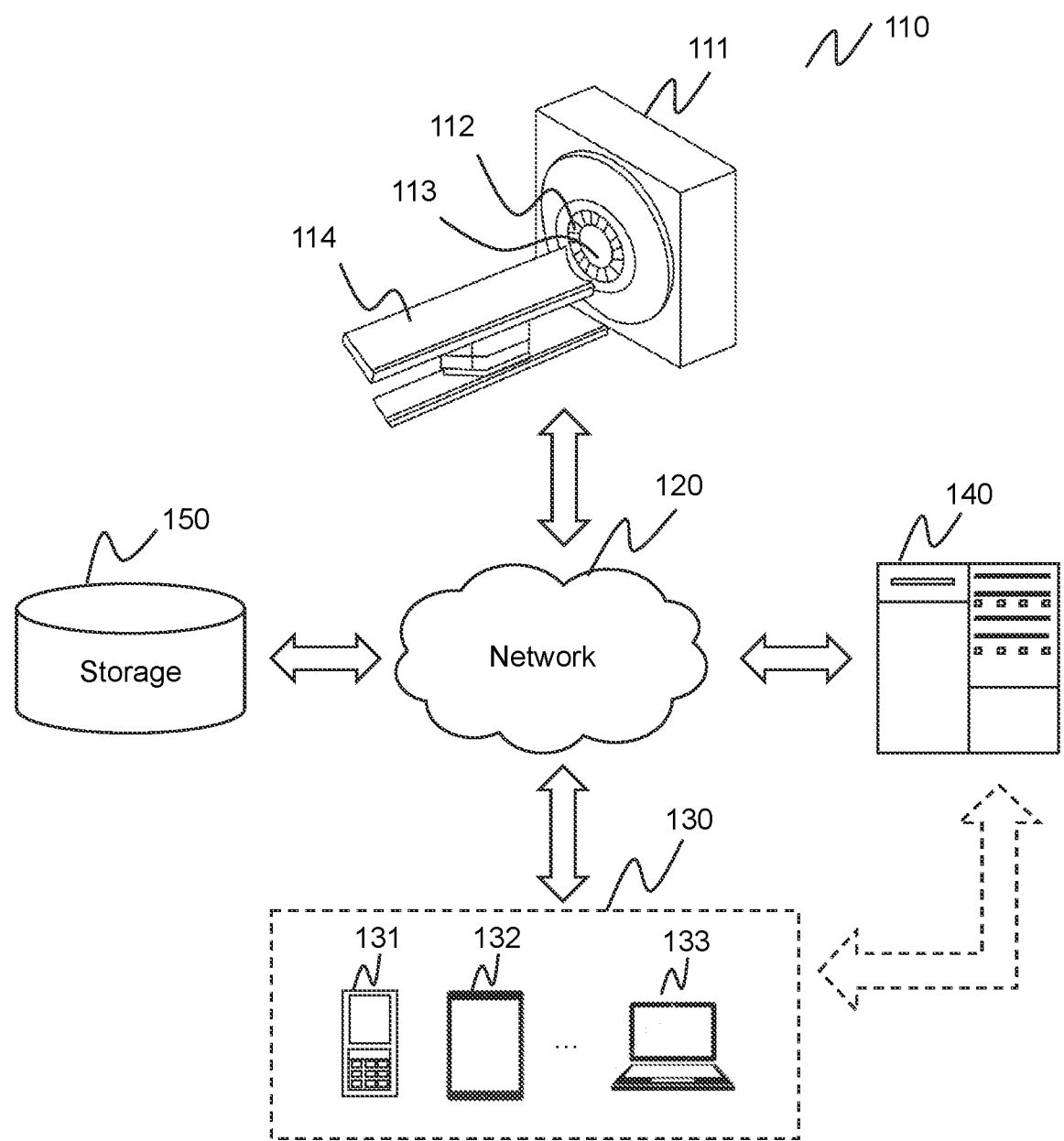
FIG. 1 is a schematic diagram illustrating an exemplary imaging system according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processing device 140 as illustrated in FIG. 1) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure may relate to systems for PET imaging. A system for PET imaging may include a gantry comprising a detection region to accommodate a subject. A plurality of detector apparatuses may be arranged along a circumferential direction of the gantry. Each of the one or more detector apparatuses may include a detecting module and an electronic module. The detecting module may include a plurality of detecting cells arranged along an axial direction of the gantry that may be perpendicular to the circumferential direction. Each of the plurality of detecting cells may be configured to generate electrical signals in response to detection of radiation rays emitted from the subject located within the detection region surrounded by the plurality of detector apparatuses. Each of the plurality of detecting cells may be detachable. It may be efficient to add, remove and/or replace the detecting cells from the PET imaging system. In addition, the system for PET imaging may further include a plurality of cooling assemblies configured to cool the plurality of detector apparatuses. In this way, the efficiency of the cooling may be increased, and the temperature variation may be decreased, which may provide a stable temperature for the PET imaging system.

FIG. 1 is a schematic diagram illustrating an exemplary imaging system 100 according to some embodiments of the present disclosure. In some embodiments, the imaging system 100 may be a single-modal system such as a positron emission tomography (PET) imaging system. Alternatively, the imaging system 100 may be a multi-modal system such as a positron emission tomography PET-CT imaging system, a PET-MRI imaging system, etc. As shown in FIG. 1, the imaging system 100 may include a scanner 110, a network 120, one or more terminals 130, a processing device 140, and a storage 150. In some embodiments, the scanner 110, the processing device 140, the storage 150, and/or the terminal(s) 130 may be connected to and/or communicate with each other via a wireless connection (e.g., the network 120), a wired connection, or a combination thereof. The connection between the components in the imaging system 100 may be variable. Merely by way of example, the scanner 110 may be connected to the processing device 140 through the network 120, as illustrated in FIG. 1. As another example, the scanner 110 may be connected to the processing device 140 directly. As a further example, the storage 150 may be connected to the processing device 140 through the network 120, as illustrated in FIG. 1, or connected to the processing device 140 directly.

The scanner 110 may scan a subject and generate scan data corresponding to the subject. In some embodiments, the scanner 110 may be a medical imaging device, for example, a PET device, a PET-CT device, a PET-MRI device, etc. The subject may include, but not limited to one or more organs (e.g., a prostate, a lung, a brain, a spine, a liver, a pancreas, a breast, etc.), one or more tissues, or the like, of a patient. The scanner 110 may include a gantry 111, a detector assembly 112, a detection region 113, a table 114, and a cooling assembly (not shown).

The gantry 111 may be configured to support one or more parts of the scanner 110, for example, the detector assembly 112, etc. The gantry 111 may include a substantially circular opening (e.g., the detection region 113) to accommodate a subject to be scanned. In some embodiments, the opening of the gantry 111 may be of another shape including, for example, an oval. The term "subject" and the term "object" are used interchangeably in the present disclosure, unless stated otherwise. The detector assembly 112 may be configured to detect radiation rays (e.g., gamma rays) emitted from the subject and generate electrical signals. In some embodiments, the detector assembly 112 may include a plurality of detector apparatuses arranged on the gantry 111 along a circumferential direction of the gantry 111. The plurality of detector apparatuses may be arranged in any structure, for example, a ring (e.g., a detector ring), a rectangle, a triangle, or an array. See, for example, FIG. 2, and the description thereof. Each of the plurality of detector apparatuses may include a detecting module, an electronics module, and a cooling assembly. The detecting module may include one or more detecting cells arranged along an axial direction of the gantry. More detailed description of the detector assembly 112 may be found elsewhere in the present disclosure, for example, FIGS. 3-5, and the description thereof. The table 114 may be configured to support a subject to be scanned and/or position the subject at a desired position in the detection region 113. The cooling assembly may cool the each of the plurality of detector apparatuses. The cooling assembly may produce, transfer, deliver, channel, or circulate a cooling medium to the scanner 110 to absorb and/or exchange heat produced by the scanner 110 during an imaging procedure. In some embodiments, the cooling assembly may be entirely integrated into the scanner 110 and become a part of the scanner 110. In some embodiments, the cooling assembly may be partially integrated into the scanner 110 and associated with the scanner 110. The cooling assembly may allow the scanner 110 to maintain a suitable and stable working temperature (e.g., 25° C., 30° C., 35° C., etc.). In some embodiments, the cooling assembly may control the temperature of one or more target components of the scanner 110. The target components may include the detector assembly 112 (e.g., a detector apparatus), and/or any other component that generates heat in operation. The cooling medium may be gaseous, liquid (e.g., water), or the like, or any combination thereof. In some embodiments, the gaseous cooling medium may be air. More descriptions of the cooling assembly may be found elsewhere in the present disclosure. See, for example, FIGS. 7, 8A and 8B and the descriptions thereof.

The network 120 may include any suitable network that can facilitate exchange of information and/or data for the imaging system 100. In some embodiments, one or more components of the imaging system 100 (e.g., the scanner 110, the terminal 130, the processing device 140, the storage 150, etc.) may communicate information and/or data with one or more other components of the imaging system 100 via the network 120. For example, the processing device 140 may obtain image data (e.g., time information, electrical/visible light signal) from the scanner 110 via the network 120. As another example, the processing device 140 may obtain user instructions from the terminal 130 via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or a combination thereof. In some embodiments, the smart home device may include a smart lighting device, a control device of an intelligent electrical device, a smart monitoring device, a smart television, a smart video camera, an interphone, or the like, or a combination thereof. In some embodiments, the wearable device may include a smart bracelet, smart footgear, a pair of smart glasses, a smart helmet, a smartwatch, smart clothing, a smart backpack, a smart accessory, or the like, or a combination thereof. In some embodiments, the smart mobile device may include a smartphone, a personal digital assistant (PDA), a gaming device, a navigation device, a point of sale (POS) device, or the like, or a combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or a combination thereof. For example, the virtual reality device and/or the augmented reality device may include a Google Glass, an Oculus Rift, a Hololens, a Gear VR, etc. In some embodiments, the terminal(s) 130 may remotely operate the scanner 110. In some embodiments, the terminal(s) 130 may operate the scanner 110 via a wireless connection. In some embodiments, the terminal(s) 130 may receive information and/or instructions inputted by a user, and send the received information and/or instructions to the scanner 110 or the processing device 140 via the network 120. In some embodiments, the terminal(s) 130 may receive data and/or information from the processing device 140. In some embodiments, the terminal(s) 130 may be omitted. In some embodiments, the terminal(s) 130 may be part of the processing device 140.

The processing device 140 may process data and/or information obtained from the scanner 110, the terminal(s) 130, and/or the storage 150. For example, the processing device 140 may process image data (including the time information, the electrical/visible light signal, etc.) and reconstruct an image based on the image data. In some embodiments, the processing device 140 may be a single server or a server group. The server group may be centralized or distributed. In some embodiments, the processing device 140 may be local or remote. For example, the processing device 140 may access information and/or data stored in the scanner 110, the terminal(s) 130, and/or the storage 150 via the network 120. For example, the processing device 140 may process visible light signal and/or visible light signal obtained from the detector assembly 112. As another example, the processing device 140 may be directly connected to the scanner 110, the terminal(s) 130 and/or the storage 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device. In some embodiments, the processing device 140, or a portion of the processing device 140 may be integrated into the scanner 110.

In some embodiments, a computing device may include a processor, a storage, an input/output (I/O), and a communication port. The processor may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. In some embodiments, the processor may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The storage 150 may store data, instructions, and/or any other information. In some embodiments, the storage 150 may store data obtained from the terminal(s) 130 and/or the processing device 140. In some embodiments, the storage 150 may store data and/or instructions that the processing device 140 may execute or use to perform exemplary methods described in the present disclosure. The storage may store data/information obtained from the scanner 110, the terminal(s) 130, and/or any other component of the imaging system 100. In some embodiments, the storage 150 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage may store one or more programs and/or instructions to perform exemplary methods described in the present disclosure. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the imaging system 100 (e.g., the processing device 140, the terminal(s) 130, etc.). One or more components in the imaging system 100 may access the data or instructions stored in the storage 150 via the network 120. In some embodiments, the storage 150 may be directly connected to or communicate with one or more other components in the imaging system 100 (e.g., the processing device 140, the terminal(s) 130, etc.). In some embodiments, the storage 150 may be part of the processing device 140.

Figure 2:
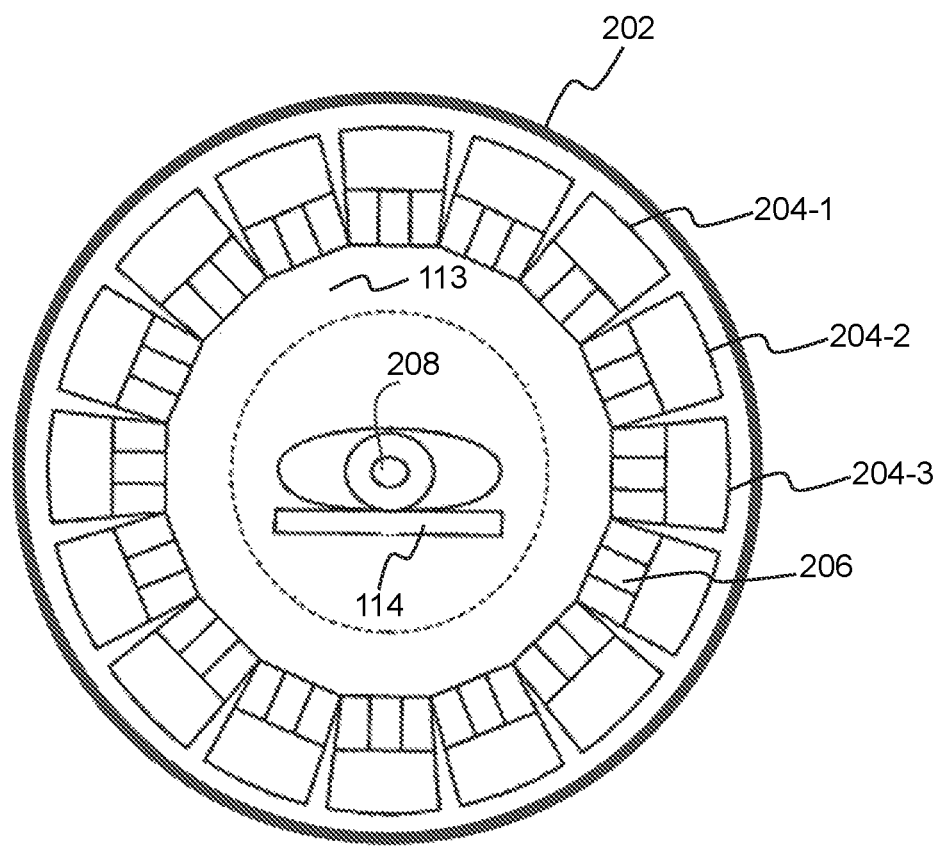
FIG. 2 is a schematic diagram illustrating a sectional view of an exemplary scanner according to some embodiments of the present disclosure.

FIG. 2 is a schematic diagram illustrating a sectional view of an exemplary scanner 110 according to some embodiments of the present disclosure. As shown in FIG. 2, a plurality of detector cassettes (e.g., a detector cassette 204-1, a detector cassette 204-2, a detector cassette 204-3, etc.) may be arranged in substantially a ring configuration (also referred to as a detector ring) in the transverse plane of the scanner 200. The plurality of detector cassettes may be covered and protected by a shell 202. In some embodiments, the shell 202 may be a hollow cylinder. The region encircled by the plurality of detector cassettes 204 may be a detection region 113. The detection region 113 may accommodate a subject 208 to be scanned. The subject 208 may be placed on the table 114. A detector cassette may include one or more detector apparatuses 206. A detector apparatus may include a detecting module and an electronics module arranged along an axial direction of the scanner 200 that is perpendicular to a circumferential direction (or the transverse plane) of the scanner 200. The detecting module may include a plurality of detecting cells. Each of the plurality of detecting cells may be configured to generate electrical signals in response to detection of annihilation photons emitted from the subject 208 located within the detection region 113 surrounded by the plurality of detector cassettes. The electronics module may be configured to process the electrical signals generated by the plurality of detecting cells. A detector may include a detecting unit and one or more electronics units configured to generate and/or process the electrical signals based on the detected annihilation photons. The detecting unit may be configured to detect the annihilation photons emitted from the subject 208. The one or more electronics units may be configured to generate and/or process the electrical signals based on the detected annihilation photons. The detailed description of the exemplary detector apparatus may be found elsewhere in the present disclosure, for example, FIGS. 3A, 3B and 4, and the description thereof.

The scanner 200 may include a cooling assembly (not shown). The cooling assembly may be integrated with each of the plurality of detector apparatuses. For example, the cooling assembly may include a plurality of cooling plates. Each of the plurality of cooling plate may be integrated into a detector apparatus to cool the detector apparatus. More descriptions of the cooling assembly may be found elsewhere in the present disclosure (e.g., FIGS. 7, 8A and 8B).

Figure 3A:
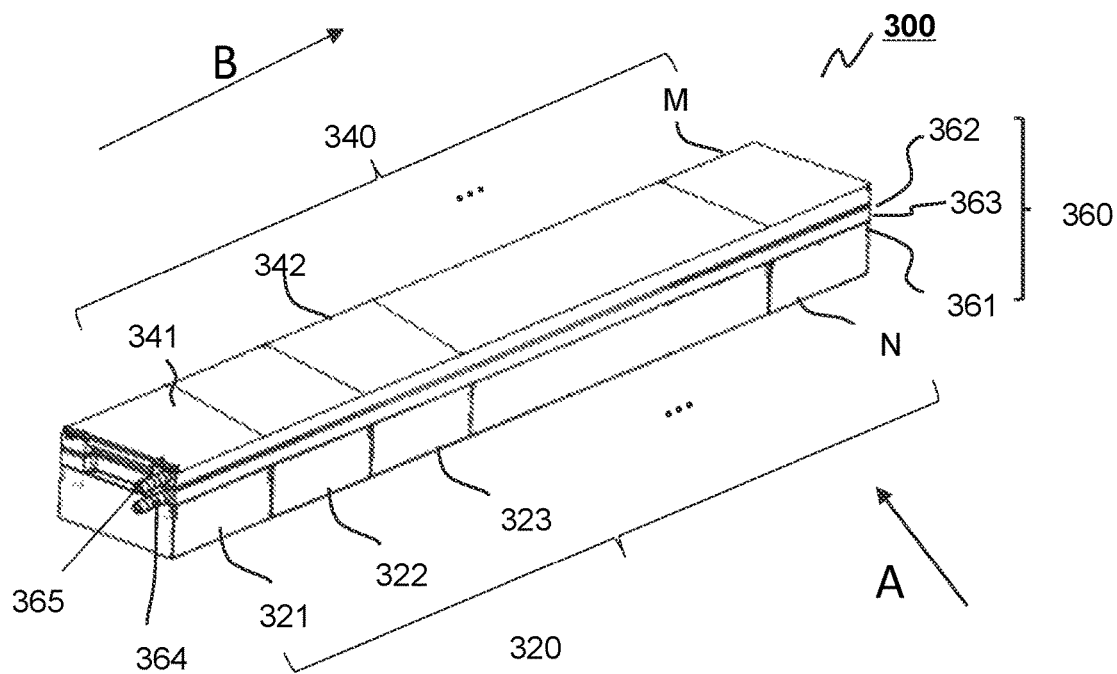
FIGS. 3A and 3B are schematic diagrams illustrating an exemplary detector apparatus according to some embodiments of the present disclosure.
Figure 3B:
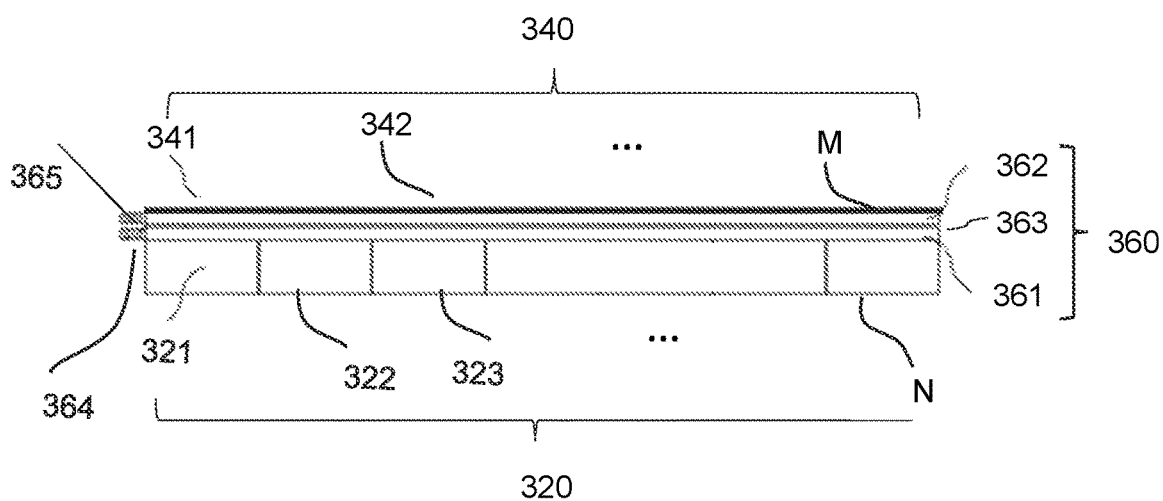

FIGS. 3A and 3B illustrate an exemplary detector apparatus 300 according to some embodiments of the present disclosure. FIG. 3B is an orthographic projection of the detector apparatus 300 in FIG. 3A viewed from a direction indicated by an arrow A. The detector apparatus 300 may include a detecting module 320, a signal processing board 340 (i.e., an electronics module), and a cooling assembly 360. The detecting module 320 may include a plurality of detecting cells, e.g., a detecting cell 321, a detecting cell 322, a detecting cell 323, . . . , a detecting cell N.

The plurality of detecting cells 320 may be arranged along the axial direction (denoted by an arrow B) of a scanner (e.g., the scanner 110 as illustrated in FIGS. 1 and 2) that is perpendicular to the circumferential direction of the scanner. In some embodiments, the number (count) of the plurality of detecting cells 320 may be in a range from 1 to 10, e.g., 3, 4, 5, 6, 7, 8, etc. In some embodiments, the number of the plurality of detecting cells 320 may exceed 10, e.g., 15, 20, etc. A detecting cell (e.g., the detecting cell 321, the detecting cell 322, the detecting cell 323, . . . , the detecting cell N) may be configured to receive radiation rays (e.g., gamma rays) and generate electrical signals based on the detected radiation rays emitted from a subject (e.g., the subject 208 located within the detection region 113). In some embodiments, the plurality of detecting cells 320 may be arranged as an array of M×N (not shown). M may denote a longitudinal direction (i.e., the axial direction of the scanner denoted by arrow B). N may denote a circumferential direction (i.e., the direction denoted by arrow A) of the scanner. M and/or N may be greater than 1. A detecting cell (e.g., the detecting cell 321, the detecting cell 322, the detecting cell 323, . . . , the detecting cell N) may include a detecting unit, an electronics unit (also referred to as first electronics unit), and a support. The support may be configured to provide a support and/or protect for the detecting unit and the first electronics unit. The detecting unit may be configured to detect the radiation rays emitted from a subject (e.g., the subject 208 located within the detection region 113) and convert the detected radiation rays into visible light signals. The detecting unit may include a crystal array. The first electronics unit may be configured to convert the visible light signals into the electrical signals. The first electronics unit may include a photosensor array. More descriptions of a detecting cell may be found elsewhere in the present disclosure, for example, FIG. 4 and the description thereof. In some embodiments, each of the plurality of detecting cells 320 (e.g., the detecting cell 321, the detecting cell 322, the detecting cell 323, . . . , the detecting cell N) may be detachable. It may be easy to detach and/or add a certain number of detecting cells from/to the detector apparatus 300. See, for example, FIG. 5 and the description thereof.

The signal processing board 340 may be connected to and/or in communication with the first electronics unit in each of the plurality of detecting cells (i.e., the detecting module 320). For example, the signal processing board 340 may be configured to receive and process electrical signals generated by the plurality of detecting cells. As a further example, the signal processing board 340 may convert the electrical signals relating to an energy of radiation rays received by the plurality of detecting cells to a digital signal. The signal processing board 340 may compare a plurality of digital signals, analyze the plurality of digital signals, and determine an interaction position and/or an interaction time of the received radiation rays in the detecting units of the plurality of detecting cells 320. The signal processing board 340 may determine one or more coincidence events based on the plurality of digital signals. The signal processing board 340 may determine image data based on the coincidence events and the energies of radiation rays recognized as the coincidence events. The imaging data may be transmitted to and processed by a processing device (e.g., the processing device 140) to generate an image. In some embodiments, the signal processing board 340 may include one or more electronics units (i.e., second electronics unit), such as a second electronics unit 341, a second electronics unit 342, . . . , a second electronics unit M, etc. In some embodiments, the number of the one or more electronics units may be in a range from 1 to 10, e.g., 3, 4, 5, 6, 7, 8, etc. In some embodiments, the number of the one or more electronics units may exceed 10, e.g., 15, 20, etc. A second electronics unit may include an adder, a multiplier, a subtractor, an amplifier, a drive circuit, a differential circuit, an integral circuit, a counter, a filter, an analog-to-digital converter (ADC), a lower limit detection (LLD) circuit, a constant fraction discriminator (CFD) circuit, a time-to-digital converter (TDC), a coincidence circuit, or the like, or any combination thereof.

In some embodiments, the number of the one or more second electronics units may be same as the number of the plurality of detecting cells 320 in the detector apparatus 300. Each of the one or more second electronics units may correspond to one of the plurality of detecting cells 320. For example, a specific second electronics unit (e.g., the second electronics unit 342) may be predetermined or adjusted to collect and process electrical signals generated by a specific detecting cell (e.g., the detecting cell 322). In some embodiments, the number of the one or more second electronics units may be smaller than the number of the plurality of detecting cells 320 in the detector apparatus 300. One single second electronics unit may be coupled to at least two of the plurality of detecting cells. For example, a second electronics unit (e.g., the second electronics unit 341) may be coupled to two of the plurality of detecting cells 320 (e.g., the detecting cell 321 and the detecting cell 322). The electrical signals generated by the two detecting cells (e.g., the detecting cell 321 and the detecting cell 322) may be transmitted to and processed by the second electronics unit (e.g., the second electronics unit 341) to generate imaging data. As another example, the one or more second electronics units may be integrated into one single electronics unit. The plurality of detecting cells 320 may be coupled to the one single electronics unit.

The cooling assembly 360 may be configured to produce, transfer, deliver, channel, or circulate the cooling medium to the detector apparatus 300 to absorb and/or exchange heat produced by the detector apparatus 300 (e.g., the plurality of detecting cells 320, the signal processing board 340, etc.) during an imaging procedure. The cooling medium may be gaseous, liquid (e.g., water), or the like, or any combination thereof. The cooling assembly 360 may allow the detector apparatus 300 to maintain a suitable and stable working temperature (e.g., 25° C., 30° C., 35° C., etc.). The cooling assembly 360 may be configured between the signal processing board 340 and the plurality of detecting cells 320. Each of the plurality of detecting cells 320 and the one or more signal processing board 340 may be connected with at least one portion of the cooling assembly 360 detachably.

The cooling assembly 360 may include one or more cooling plates, one or more inlets and one or more outlets connected with the one or more cooling plates. The one or more cooling plates may include a heat conduction material, for example, a metal material, a ceramic material, or any other non-metal material having a good heat conductivity. Exemplary metal materials may include silver, copper, aluminum, etc. In some embodiments, the cooling assembly 360 may include one single cooling plate. The one single cooling plate may include a first layer 361 and a second layer 362. The first layer 361 and the second layer 362 may be part of made of the one single cooling plate. For example, the one single cooling plate may be made using a pouring technique to form the first layer 361 and the second layer 362. The first layer 361 may be configured to cool the plurality of detecting cells 320. The first layer 361 may be thermally connected with the plurality of detecting cells 320. The first layer 361 may be configured with a first flow channel. The second layer 362 may be configured to cool the signal processing board 340. The second layer 362 may be thermally connected with the signal processing board 340. The second layer 362 may be configured with a second flow channel. The first flow channel and the second flow channel may be configured to accommodate a cooling medium. In some embodiments, the first layer 361 and the second layer 362 may be in flow communication. The cooling medium may flow from the first flow channel to the second flow channel. For example, the cooling assembly 360 may include an inlet 364 mounted on the first layer 361 and an outlet 365 mounted on the second layer 362. The cooling medium may flow into the first layer 361 via the inlet 364 to cool the plurality of detecting cells 320. The cooling medium may further flow from the first layer 361 into the second layer 362 via a connector to cool the signal processing board 340. The heated cooling medium may flow out of the second layer 362 via the outlet 365. In some embodiments, the first layer 361 and the second layer 362 may be not in flow communication. The cooling medium may flow in the first flow channel and the second flow channel independently. For example, each of the first layer 361 and the second layer 362 may be connected with an inlet and an outlet. The cooling medium may flow into the first layer 361 and the second layer 362 via the inlet associated with each of the first layer 361 and the second layer 362, respectively. The heated cooling medium after absorbing heat generated by the plurality of detecting cells 320 and the signal processing board 340 may flow out of the first layer 361 and the second layer 362 via the outlet associated with each of the first layer 361 and the second layer 362, respectively.

The first layer 361 and the second layer 362 may be thermally disconnected from each other to prevent and/or reduce heat exchange between the first layer 361 and the second layer 362. For example, at least a portion of the first layer 361 and the second layer 362 may be separated from each other physically. As a further example, a thermally insulating layer 363 may be configured between the first layer 361 and the second layer 362. The thermally insulating layer 363 may be configured to insulate the first layer 361 and the second layer 362 physically, and avoid and/or decrease heat exchange between the first layer 361 and the second layer 362. In some embodiments, the thermally insulating layer 363 may include a thermally insulating material with a heat conductivity smaller than a threshold (e.g., 0.2 W/(m·K)), such as fiber, plastic (e.g., acrylonitrile-butadiene-styrene (ABS), polyformaldehyde (POM), etc.), rubber, resin, etc. In some embodiments, the thermally insulating layer 363 may include a gas, such as air, nitrogen, etc. In some embodiments, the thermally insulating layer 363 may be a vacuum layer. The first layer 361 and/or the second layer 362 may be formed with the one single cooling plate using a whole shaped technique, for example, incising the one single cooling plate.

In some embodiments, the cooling assembly 360 may include at least two cooling plates, such as a first cooling plate and a second cooling plate. The first cooling plate may be thermally connected with and configured to cool the plurality of detecting cells 320. The second cooling plate may be thermally connected with and configured to cool the signal processing board 340. The cooling assembly 360 may also include a thermally insulating plate (or layer). The first cooling plate, the second cooling plate, and the heat insulting plate may be connected with each other via one or more connectors. The first cooling plate may be same as or similar with the first layer 361. The second cooling plate may be same as or similar with the second layer 362. The thermally insulating plate may be same as or similar with the thermally insulating layer 363. More detailed description of the cooling assembly may be found elsewhere, for example, FIGS. 8A and 8B, and the descriptions thereof.

It should be noted that the above descriptions of the diagram in FIGS. 3A-3B are merely provided for the purposes of illustration, and not intended to limit the scope of the present disclosure. For persons having ordinary skills in the art, multiple variations or modifications may be made under the teachings of the present disclosure. For example, the cooling assembly may further include other components, such as a refrigerator, a pump, a control module, a valve, etc. However, those variations and modifications do not depart the scope of the present disclosure.

Figure 4:
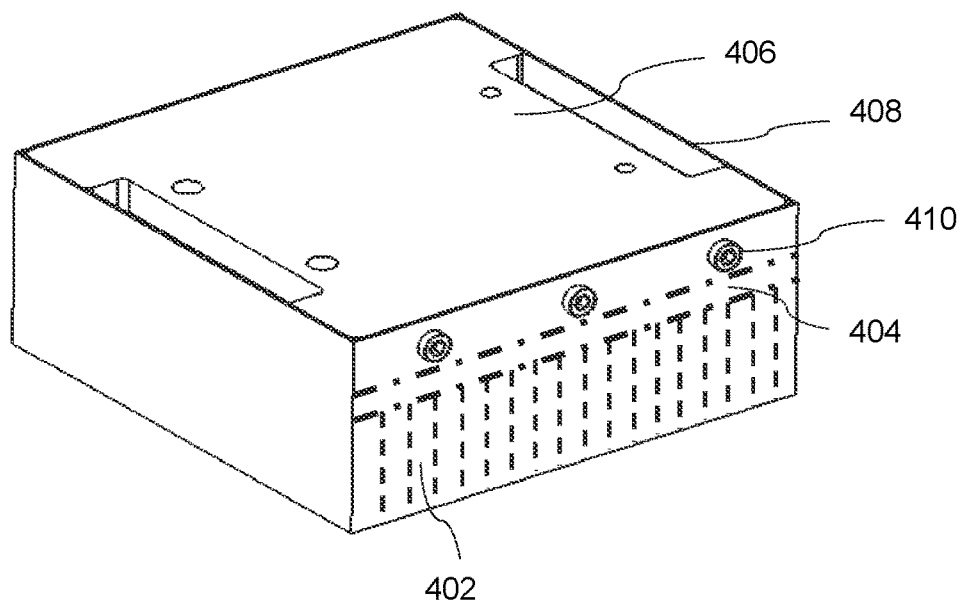
FIG. 4 is a schematic diagram illustrating an exemplary detecting cell according to some embodiments of the present disclosure.

FIG. 4 is a schematic diagram illustrating an exemplary detecting cell 400 according to some embodiments of the present disclosure. As shown in FIG. 4, the detecting cell 400 may include a detecting unit 402, an electronics unit 404, a base 406, and a shell 408. In some embodiments, a shape of the detecting cell 400 may include, a rectangle, a square, etc.

The detecting unit 402 may include a crystal array. In some embodiments, the crystal array may include one or more scintillators. A scintillator may scintillate when a radiation ray (e.g., γ ray) photon impinging on the scintillator. The scintillator may absorb the energy of the radiation ray (e.g., γ ray) photon, and convert the absorbed energy into visible light signals. In some embodiments, the scintillators of the scintillator array may be arranged in N rows and M columns. N may be an integer larger than 0. M may be an integer larger than 0. In some embodiments, N may be equal to M. In some embodiments, N may be different from M. In some embodiments, the N×M scintillator array may be obtained by making partial cuts through a crystal with a saw. In some embodiments, the cuts may be made to various depths. In some embodiments, two adjacent scintillators of the scintillator array may be filled with a barrier material (e.g., a light-reflective film, etc.). The scintillator may use one or more types of crystals including, for example, NaI (Tl), BGO, LSO, YSO, GSO, LYSO, LaBr3, LFS, LuAP, LuI3, BaF2, CeF, CsI(Tl), CsI(Na), CaF2(Eu), CdWO4, YAP, or the like, or any combination thereof. Alternatively or additionally, the detecting unit 402 may include a semiconductor element configured to convert a radiation ray (e.g., γ ray) photon impinging on the semiconductor element into the visible light signals. The semiconductor element may be made of semiconductor material, for example, CdTe (cadmium telluride), TlBr (thallium bromide), and GaAS (gallium arsenide), or the like, or any combination thereof.

In some embodiments, the electronics unit 404 may include a photosensor array. The photosensor array may include a plurality of photosensors configured to convert the visible light signals (e.g., the light output from a scintillator) into electrical signals. In some embodiments, a photosensor may be a photomultiplier tube (PMT), a silicon photomultiplier (SiPM), etc. In some embodiments, a photosensor (e.g., PMT, or SiPM) may be a single-channel photosensor or a multi-channel photosensor. In some embodiments, a photosensor may be coupled to one or more scintillators of the scintillator array simultaneously. In some embodiments, the photosensor array may be arranged on a first surface or a second surface of the scintillator array. In some embodiments, two photosensor arrays may be arranged on the first surface and the second surface of the scintillator array, respectively. In some embodiments, the photosensors of the photosensor array may be arranged in N' rows and M' columns. N' may be an integer larger than 0 but no larger than N. M' may be an integer larger than 0 but no larger than M. In some embodiments, the photosensor may be coupled to one or more scintillators of the scintillator array simultaneously.

The base 406 and/or the shell 408 may provide support and/or protection for the detecting unit 402 and the electronics unit 404. The base 406 and/or the shell 408 may be also referred to as a supporting assembly. For example, the electronics unit 404 may be connected with a component of a cooling assembly (e.g., the first layer 361 of the cooling assembly 360) detachably via the base 406. As another example, the shell 408 may provide a confined space to accommodate the detecting unit 402 and electronics unit 404. In some embodiments, the detecting unit 402 may be connected with the electronics unit 404. The electronics unit 404 may be mounted on the base 406. The base 406 may be connected with other components of a detector apparatus (e.g., the cooling assembly 360 of the detector apparatus 300) via one or more connecting mechanisms. The shell 408 may be connected with the base 406 via one or more connecting mechanisms. Exemplary connecting mechanisms may include using welding, bonding, riveting, clamping, bolting, pin joint, etc. For example, the shell 408 may be connected with the base 406 via one or more fasteners 410. The fasteners 410 may include screws, rivets or any other suitable type fasteners to connect the base 406 with the shell 408.

The base 406 and/or the shell 408 may include a heat conductivity material with a heat conductivity greater than a threshold (e.g., 10 W/(m·K)), such as a metal material, a ceramic material, a graphene material, or any other non-metal material having a good heat conductivity, such that heat generated by the detecting cell 400 may be conducted to a cooling assembly (e.g., the first layer 361 of the cooling assembly 360) via the base 406 and/or the shell 408. Exemplary metal materials may include silver, copper, aluminum, aluminum nitride (AlN), etc. In some embodiments, the shell 408 may be made of a material with a low density smaller than a threshold (e.g., 2 g/cm$^3$), such as fiber (e.g., carbon fiber), plastic, etc.

Figure 5:
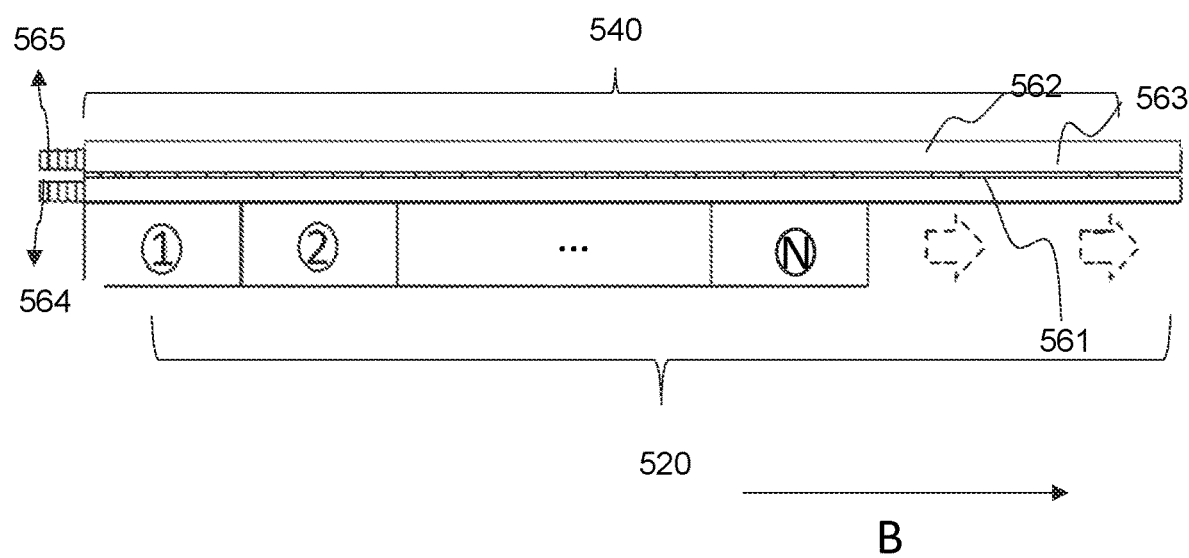
FIG. 5 is a schematic diagram illustrating an exemplary detector apparatus according to some embodiments of the present disclosure.

FIG. 5 is a schematic diagram illustrating an exemplary detector apparatus 500 according to some embodiments of the present disclosure. The detector apparatus 500 may include a detecting module 520 including a plurality of detecting cells, a signal processing board 540, and a cooling assembly. The cooling assembly may include a first cooling plate 561, a second cooling plate 562, a thermally insulating layer 563, an inlet 564 and an outlet 565 as described elsewhere in the present disclosure (e.g., FIG. 3A and the descriptions thereof).

As shown in FIG. 5, the plurality of detecting cells (e.g., a detecting cell 1, detecting cell 2, . . . , detecting cell N, etc.) of the detecting module 520 may be arranged in the detector apparatus 500 along the along an axial direction (denoted by arrow B) of a scanner (e.g., the gantry 111) that is perpendicular to a circumferential direction of the scanner. Each of the plurality of detecting cells may be connected with the first cooling plate 561 detachably via one or more connecting mechanisms. Exemplary connecting mechanisms may include using riveting, clamping, bolting, pin joint, etc. Thus, a number (count) of the plurality of detecting cells of the detecting module 520 in the detector apparatus 500 may be adjustable. The number of the plurality of detecting cells in the detector apparatus 500 may relate to the axial length of the detector apparatus 500. The greater the number of the plurality of detecting cells in the detector apparatus 500 is, the greater the axial length of the detector apparatus 500 may be. The axial length of the detector apparatus 500 may relate to an axial field-of-view (AFOV) of a scanner (e.g., the scanner 110). As used herein, the AFOV may refer to a maximum length along the axial direction of the scanner (e.g., the scanner 110) to detect a coincidence event effectively. The greater the axial length of the detector apparatus 500 is, the larger the AFOV of the scanner 110 may be. For instance, the axial length of the detector apparatus 500 may be in a range from 0.75 meters to 2 meters.

The number of the plurality of detecting cells in the detecting module 520 may be adjusted and/or set by a user (e.g., an operator) according to clinical demands. For example, for a multiple organs scan (e.g., a head, a heart, a lung, a liver, a stomach, a pancreas, a bladder, a knee, etc.) or a whole-body scan of a subject that may be achieved in a single scan, a larger AFOV of a scanner (e.g., the scanner 110) may be needed, which may need more detecting cells arranged along the axial direction of the scanner (e.g., the scanner 110). As another example, for a local scan (e.g., a head, a heart, a lung, a liver, a stomach, a pancreas, a bladder, a knee, etc.) of a subject, or a whole-body scan of a subject with a small size (e.g., a child), a smaller AFOV of a scanner (e.g., the scanner 110) may be needed, which may need less detecting cells arranged along the axial direction of the scanner. As a further example, the detector module 520 may include N detecting cells (detecting cell 1, detecting cell 2, . . . , detecting cell N) for a local scan (e.g., a head, a heart, a lung, a liver, a stomach, a pancreas, a bladder, a knee, etc.) of a subject. As still another example, the detector module 520 may be additionally configured with detecting cell N+1 and/or detecting cell N+2 for a multiple organs scan (e.g., a head, a heart, a lung, a liver, a stomach, etc.).

According to the present disclosure, each detecting cell of the plurality of detecting cells may be removed from or installed on the detecting module 520 separately and detachably. Thus if any one of the plurality of detecting cells does not work, it may be convenient to repair or replace the faulted detecting cell by detaching the faulted detecting cell from the detecting module. Additionally, one or more detecting cells may be added to or detached from the detecting module 520 according to clinical demands, which may improve efficiency and quality of imaging.

The signal processing board 540 may be connected to and/or in communication with the plurality of detecting cells 520 as described elsewhere in the present disclosure (e.g., FIG. 3A and the descriptions thereof). For example, the signal processing board 540 may be configured to receive and process electrical signals generated by the detecting module 520 (e.g., the plurality of detecting cells). The signal processing board 540 may include one or more electronics units (i.e., second electronics units) as described in connection with FIG. 3A. Each of the one or more second electronics units may be connected with the second cooling plate 562 of the cooling assembly detachably via one or more connecting mechanisms as described elsewhere in the present disclosure. Thus the number of the signal processing board 540 may be adjustable according to the number of the plurality of detecting cells. For example, if the detector apparatus 500 (i.e., the detecting module 520) is added with detecting cell 6 and/or detecting cell 7, the signal processing board 540 may be added with additional electronics units. According to the present disclosure, each of the one or more second electronics units may be detached from and/or added to the detector apparatus 500 (i.e., the detecting module 520) independently. Thus if any one of the one or more second electronics units in the signal processing board 540 does not work, it may be convenient to repair or replace the faulted second electronics unit by detaching the faulted second electronics unit from the detecting module 520). Additionally, one or more second electronics units may be added to or detached from the detector apparatus 500 according to the number of the plurality of detecting cells, which may improve efficiency and quality of imaging.

In some embodiments, each of the one or more second electronics units may be associated with one of the plurality of detecting cells. For example, a specific second electronics unit may be predetermined or adjusted to collect and process electrical signals generated by a specific detecting cell (e.g., detecting cell 1) associated with the specific electronics unit. In some embodiments, at least one of the one or more second electronics units may be associated with at least two of the plurality of detecting cells. For example, a second electronics unit (e.g., the second electronics unit 306-1) of the one or more second electronics units may be coupled to two of the plurality of detecting cells e.g., detecting cell 1 and detecting cell 2). The electrical signals generated by the two detecting cells (e.g., detecting cell 1 and detecting cell 2) may be transmitted to the second electronics unit and the electrical signals may be processed by the second electronics unit (e.g., the second electronics unit 306-1) to generate imaging data.

The first cooling plate 561 may be configured to cool the plurality of detecting cells 520. The second cooling plate 562 may be configured to cool the signal processing board 540. In some embodiments, the thermally insulating layer 563 may be disposed between the first cooling plate 561 and the second cooling plate 562. The thermally insulating layer 563 may be configured to prevent and/or decrease heat exchange between the first cooling plate 561 and the second cooling plate 562. The inlet 564 may be mounted on the first cooling plate 561. The outlet 565 may be mounted on the second cooling plate 562. A cooling medium may be injected into the first cooling plate 561 via the inlet 564, e.g., by a pump (not shown). The cooling medium absorbing heat generated by the plurality of detecting cells 520 may flow into the second cooling plate 562 via a connector between the first cooling plate 561 and the second cooling plate 562. The cooling medium may further absorb heat generated by the signal processing board 540 and flow out of the second cooling plate 562 via the inlet 564. In some embodiments, the first cooling plate 561, the second cooling plate 562, and/or the thermally insulating layer 563 may be connected together by an adhesive or with one or more fasteners. The one or more fasteners may include a threaded connector, a flanged connector, a welded connector, a socketed connector, etc. More descriptions of the cooling assembly may be found elsewhere in the present disclosure (e.g., FIGS. 7, 8A and 8B, and the descriptions thereof).

An axial length of the cooling assembly (i.e., an axial length of the first cooling plate 561, the second cooling plate 562, and/or the thermally insulating plate 563) in the axial direction may be equal to or greater than an axial length of the plurality of detecting cells (i.e., the detecting module 520), such that the cooling assembly (e.g., the first cooling plate 561) may cover the plurality of detecting cells 520 in the axial direction. An axial length of the cooling assembly (i.e., an axial length of the first cooling plate 561, the second cooling plate 562, and/or the thermally insulating plate 563) in the axial direction may be equal to or greater than an axial length of the signal processing board 540, such that the cooling assembly (e.g., the second cooling plate 562) may cover the signal processing board 540 in the axial direction. Additionally, if the detector apparatus 500 needs more detecting cells arranged along the axial direction, the cooling assembly may cover and/or cool the additional detecting cells.

It should be noted that the above descriptions of the diagram in FIG. 5 are merely provided for the purposes of illustration, and not intended to limit the scope of the present disclosure. For persons having ordinary skills in the art, multiple variations or modifications may be made under the teachings of the present disclosure. For example, the cooling assembly may further include an inlet mounted on the second cooling plate 562 and an outlet mounted on the first cooling plate 561, etc. However, those variations and modifications do not depart the scope of the present disclosure.

Figure 6A:
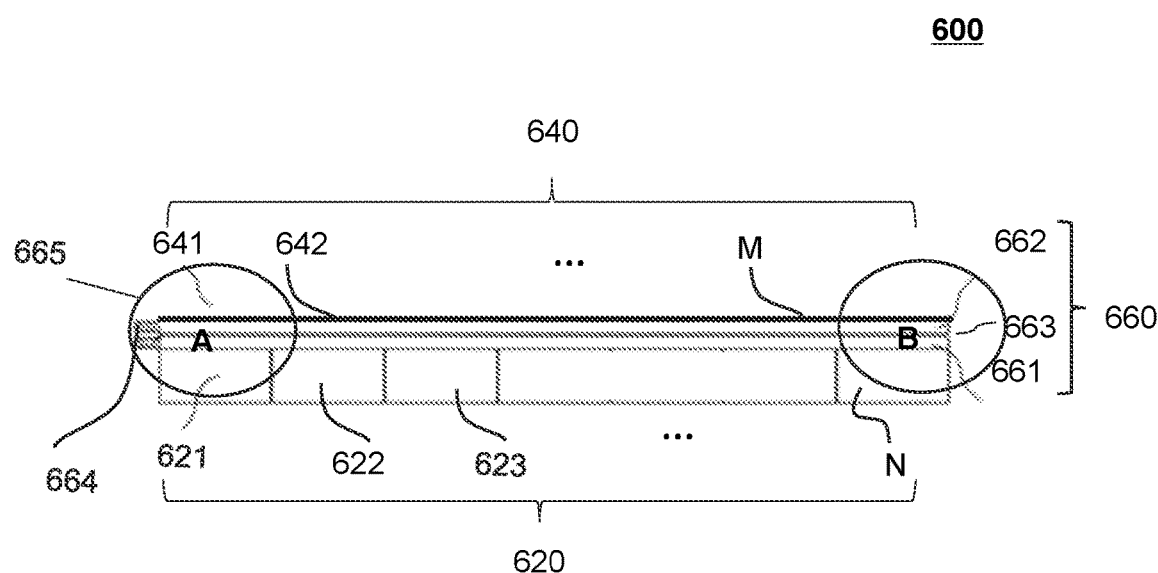
FIGS. 6A-6D are schematic diagrams illustrating an exemplary detector apparatus according to some embodiments of the present disclosure.
Figure 6B:
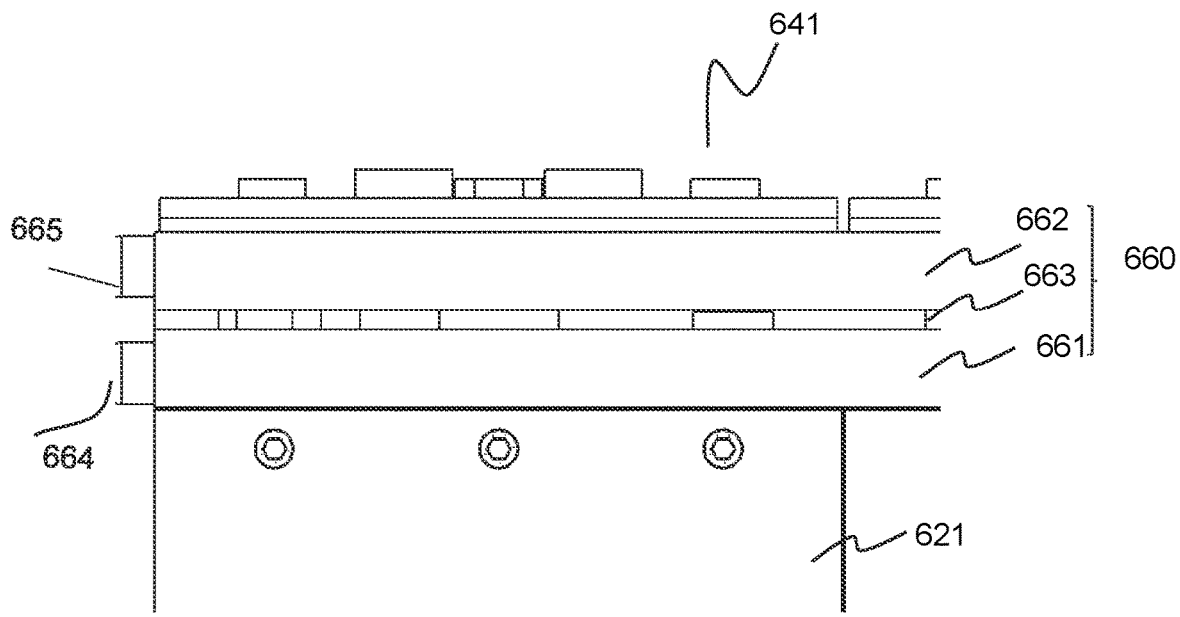
Figure 6C:
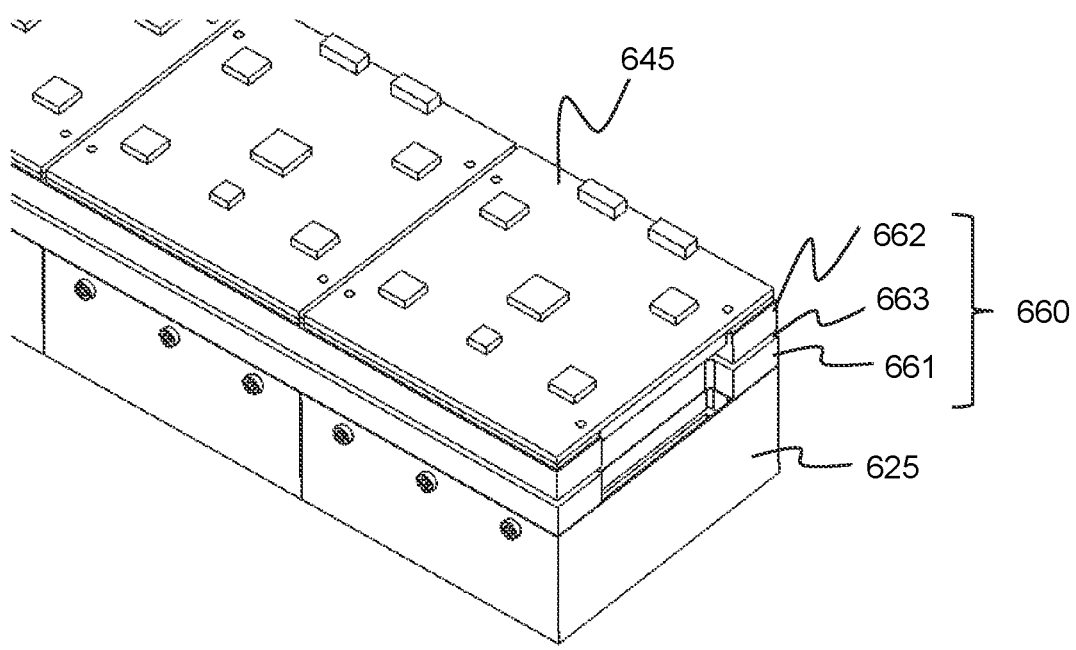
Figure 6D:
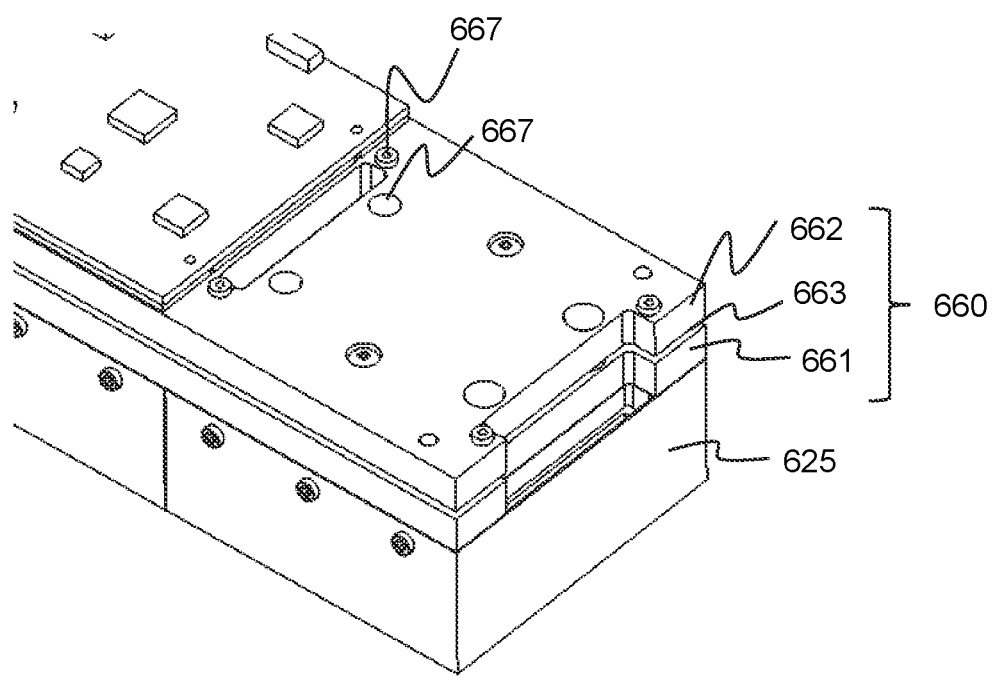

FIG. 6A is a schematic diagram illustrating an exemplary detector apparatus 600 according to some embodiments of the present disclosure. FIG. 6B is an enlarged schematic diagram of a circled portion "A" of the detector apparatus 600 in FIG. 6A. FIGS. 6C and 6D are enlarged schematic diagrams of a circled portion "B" of the detector apparatus 600 in FIG. 6A according to some embodiments of the present disclosure. The detector apparatus 600 may be similar with the detector apparatus 300 as described in FIG. 3A and/or the detector apparatus 500 as described in FIG. 5. For example, the detector apparatus 600 may include a detecting module 620 including a plurality of detecting cells (e.g., a detecting cell 621, a detecting cell 622, a detecting cell 623, . . . , a detecting cell N) and a signal processing board 640 including, e.g., an electronics unit 641, an electronics unit 642, . . . , an electronics unit M arranged detachably along an axial direction of a scanner including the detector apparatus 600.

As another example, the detector apparatus 600 may include a cooling assembly 660 located between the detecting module 620 and the plurality of signal processing board 640. The cooling assembly 660 may include a first cooling plate 661 and a second cooling plate 662. The first cooling plate 661 may be connected with the plurality of detecting cells 620. The second cooling plate 662 may be connected with the plurality of signal processing board 640. The cooling assembly may further include a thermally insulating layer 663 as shown in FIG. 6B between the first cooling plate 661 and the second cooling plate 662, an inlet 664 and an outlet 665 as described elsewhere in the present disclosure.

As still an example, each of the plurality of detecting cells (e.g., the detecting cell 621 as shown in FIG. 6B, a detecting cell 625 as shown in FIGS. 6C and 6D) of the detecting module 620 may be associated with one of the plurality of signal processing board 640 (e.g., the electronics unit 641 as shown in FIG. 6B, an electronics units as shown in FIGS. 6C and 6D). As shown in FIG. 6C, the electronics unit 645 may be connected with the second cooling plate 662 via one or more fasteners 667 as shown in FIG. 6D. The one or more fasteners 667 may include a threaded or an unthreaded fastener, or other suitable mechanical structures. As shown in FIG. 6D, the electronics unit 645 illustrated in FIG. 6C may be detached from the detector apparatus 600 based on the one or more fasteners 667. Therefore, each of the one or more second electronics units of signal processing board 640 may be detached from the detector apparatus 600 which may be convenient to repair and maintenance the signal processing board 640.

Figure 7:
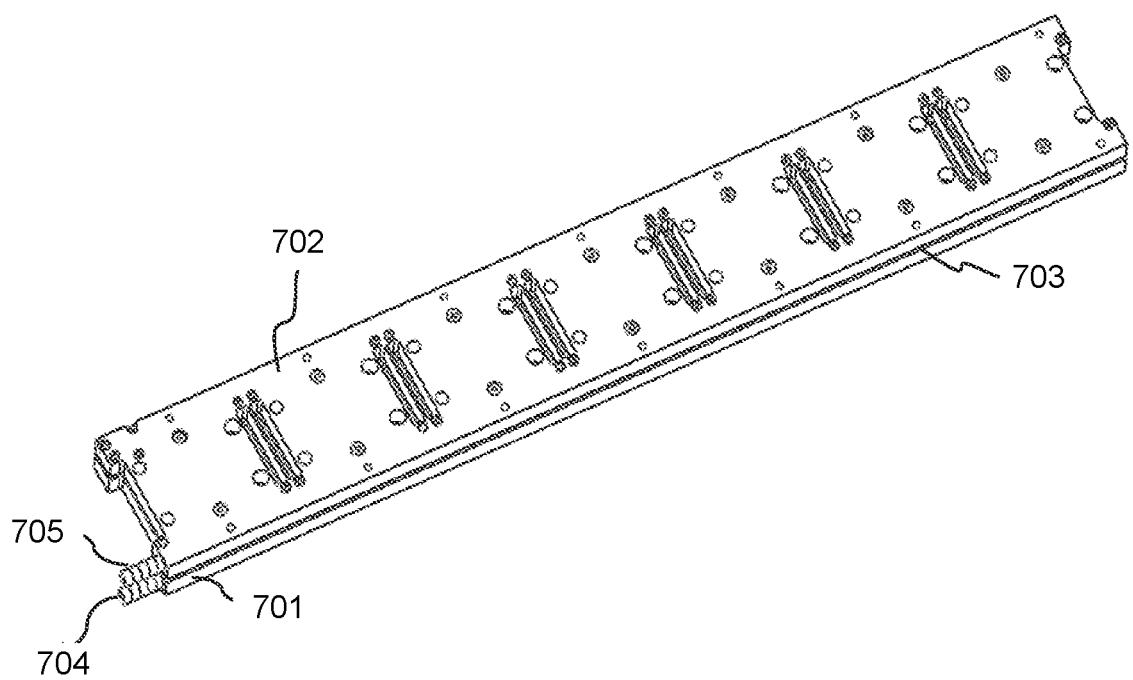
FIG. 7 is a schematic diagram illustrating an exemplary cooling assembly according to some embodiments of the present disclosure.

FIG. 7 is a schematic diagram illustrating an exemplary cooling assembly 700 according to some embodiments of the present disclosure. The cooling assembly 700 may be configured to cool components (e.g., the plurality of detecting cells 320, the signal processing board 340, etc.) of a detector apparatus (e.g., the detector apparatus 300) of a scanner (e.g., the scanner 110) during an imaging procedure. The cooling assembly 700 may allow the detector apparatus to maintain a suitable and stable working temperature (e.g., 25° C., 30° C., 35° C., etc.). At least one portion of the cooling assembly 700 may be located between components (e.g., the signal processing board 340 and the detecting module 320) of the detector apparatus (e.g., the detector apparatus 300).

As shown in FIG. 7, the cooling assembly 360 may include a first cooling plate 701, a second cooling plate 702, and a heat-insulating 703. The first cooling plate 701 may be configured to cool a detecting module (e.g., the detecting module 320) of a detector apparatus (e.g., the detector apparatus 300 as illustrated in FIG. 3A). The second cooling plate 702 may be configured to cool a signal processing board (e.g., the signal processing board 340) of the detector apparatus (e.g., the detector apparatus 300 as illustrated in FIG. 3A). The first cooling plate 701 and/or the second cooling 702 may include a material with high heat conductivity, for example, aluminum, copper, aluminum nitride (AlN), graphene, or any other material with a heat conductivity higher than a threshold (e.g., 10 W/(m*k)). The material of the first cooling plate 701 and the second cooling plate 702 may be same or different.

The first cooling plate 701 and the second cooling plate 702 may be configured with a first flow channel and a second flow channel (not shown), respectively. The first flow channel and the second channel may be configured to accommodate one or more cooling mediums. In some embodiments, the first flow channel and the second flow channel may be in flow communication, for example, via one or more connectors. The one or more cooling mediums may flow from the first flow channel into the second flow channel after absorbing heat generated by the plurality of detecting cells. In some embodiments, the first flow channel may be not in flow communication or connect with the second flow channel. In other words, the one or more cooling mediums may flow in the first flow channel and the second flow channel independently. The first flow channel may be configured to accommodate a first cooling medium, and the second flow channel may be configured to accommodate a second cooling medium. The first cooling medium and the second cooling medium may be same or different. Exemplary cooling mediums may include water, oil, polyalkylene glycol (PAG), gutting fluid, nanofluid (e.g., CuO, alumina, titanium, carbon nanotubes, etc.), liquid gas (e.g., $CO_2$), freon, etc. A flow resistance of a cooling medium (e.g., the first cooling medium) in the first flow channel may be less than or equal to a flow resistance of a cooling medium (e.g., the second cooling medium) in the second flow channel. The first flow channel and/or the second flow channel may have a curved shape, a spiral shape, a straight line shape, a serpentine shape, and a rectangular shape, or other eligible shape. The shape of the first flow channel may be same with or different from a shape of the second flow channel. For example, the first flow channel may have a curved shape, and the second flow channel may have a curved shape. As another example, the first flow channel may have a curved shape, and the second flow channel may have a serpentine shape. More descriptions of configuration of the flow channel in each of the first cooling plate 701 and the second cooling plate 702 may be found in FIGS. 8A and 8B, and the descriptions thereof.

In some embodiments, the cooling assembly 700 may further include a thermally insulating layer 703 located between the first cooling plate 701 and the second cooling plate 702. The thermally insulating layer 703 may be configured to prevent and/or decrease heat exchange between the first cooling plate 701 and the second cooling plate 702. The thermally insulating layer 703 may be made of a thermally insulating material, for example, an acrylonitrile butadiene styrene (ABS) material, a polypropylene (PP) material, a fibrous material, or the like, or the combination thereof. Alternatively or additionally, the thermally insulating layer 703 may be filled with gas, such as air, inert gas, or the like, or any combination thereof. In some embodiments, the thermally insulating layer 703 may be a vacuum layer. The first cooling plate 701, the second cooling plate 702, and the thermally insulating layer 703 may be connected with each other via one or more fasteners or by an adhesives as described elsewhere in the present disclosure (e.g., FIGS. 6A-6D and the descriptions thereof).

The cooling assembly 700 may further include one or more inlets and one or more outlets. In some embodiments, the cooling assembly 700 may include one single inlet 704 connected with the first cooling plate 701 and one single outlet 705 connected with the second cooling plate 702. A cooling medium may flow into the first flow channel in the first cooling plate 701 to absorb heat generated by the detecting module (e.g., the plurality of detecting cells) in the detector apparatus. The heated cooling medium after cooling the detecting module (e.g., the plurality of detecting cells) detecting cells may flow into the second flow channel of the second cooling plate 702 to absorb heat generated by the signal processing board of the detector apparatus and flow out of the second cooling plate 702 via the inlet 704. In some embodiments, each of the first cooling plate 701 and the second cooling plate 702 may include an inlet and an outlet. The inlet and the outlet may be connected with the two ends of each of the first cooling plate 701 and the second cooling plate 702, respectively. The cooling medium may flow into the flow channel of each of the first cooling plate 701 and the second cooling plate 702 via the inlet thereof and flow out of each of the first cooling plate 701 and the second cooling plate 702 via the outlet thereof.

In some embodiments, the cooling assembly 700 may further include a pump, a refrigerator, a control module, etc. The pump may drive the one or more cooling mediums to flow in the cooling assembly cyclically. In some embodiments, the pump may include a positive displacement pump, an impulse pump, a velocity pump, a gravity pump, a steam pump, a valveless pump, a centrifugal pump, or the like, or a combination thereof. The refrigerator may be configured to cool the used one or more cooling medium generated after absorbing heat generated by the detecting module (e.g., the plurality of detecting cells) detecting cells and the one or more electronics modules of the detector apparatus. The control module may control the pump and the refrigerator. For example, the control module may control the pump to increase or decrease flow velocity of a cooling medium in the first flow channel and/or the second flow channel.

It should be noted that the above descriptions of the diagram in FIG. 7 are merely provided for the purposes of illustration, and not intended to limit the scope of the present disclosure. For persons having ordinary skills in the art, multiple variations or modifications may be made under the teachings of the present disclosure. For example, the first cooling plate 701 and the second cooling plate 702 may be integrated into one single cooling plate. The single one cooling plate may be divided into a first layer and a second layer. However, those variations and modifications do not depart the scope of the present disclosure.

Figure 8A:
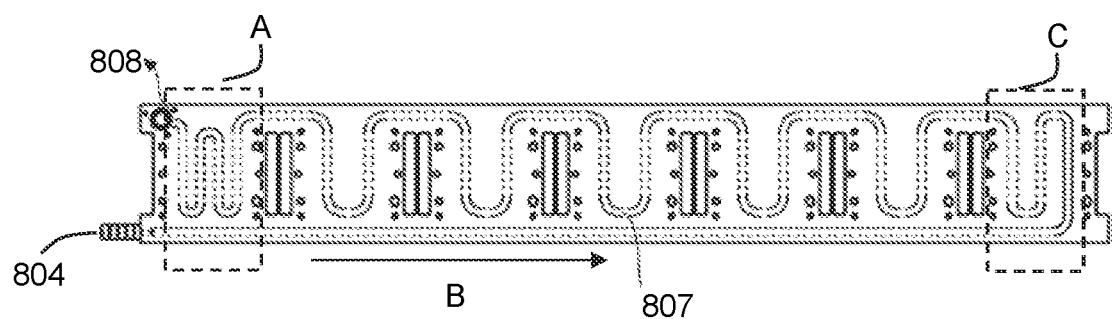
FIGS. 8A and 8B are schematic diagrams illustrating an exemplary cooling plate according to some embodiments of the present disclosure.

FIG. 8A is a schematic diagram illustrating an exemplary cooling plate 800 according to some embodiments of the present disclosure. As shown in FIG. 8A, the cooling plate 800 may include an inlet 804 and a flow channel 807. The inlet 804 may be mounted at a first end of the cooling plate 800. The flow channel 807 may be in flow communication with a refrigerator (not shown) via the inlet 804. For example, the refrigerator may generate a cooling medium. The cooling medium may be driven by a pump to flow into the flow channel 807. In some embodiments, the flow channel 807 may be in flow communication with the refrigerator (not shown) via an outlet connected with a second end of the cooling plate 800. For example, the used cooling medium after cooling the signal processing board may flow into the refrigerator via the outlet. The flow channel 807 may be configured to transfer, deliver, channel, or circulate a cooling medium to absorb heat produced by a component of a detector apparatus with a low energy consumption and/or uniform heating, such as a detecting module (e.g., a plurality of detecting cells) of the detector apparatus (e.g., the detector apparatus 300 in FIG. 3, the detector apparatus 500 in FIG. 5, and/or the detector apparatus 600 in FIG. 6,) during an imaging procedure.

In some embodiments, the flow channel 807 may have a curved shape, a spiral shape, a straight line shape, a serpentine shape, a rectangular shape, or other eligible shape, or any combination thereof. For example, the flow channel 807 may have a spiral shape arranged along the long axis direction (denoted by arrow B) of the cooling plate 800. In some embodiments, the flow channel 807 may have multiple layers. For example, the flow channel 807 may include a first layer having a straight line shape and a second layer having a curved shape. The first layer of the flow channel 807 may extend along the long axis direction (denoted by arrow B) of the cooling plate 800 from the first end to a second end of the cooling plate 800. The second layer of the flow channel 807 may cover each of the plurality of detecting cells in the detecting module (e.g., the detecting module 320 illustrated in FIG. 3A) with U-shape from the second end to the first end of the cooling plate 800.

In some embodiments, a cooling medium may flow in the flow channel 807 from the first end of the cooling plate 800 corresponding to the inlet 804 to the second end of the cooling plate 800 to absorb heat generated by the plurality of detecting cells and then flow out of the cooling plate 800. In a process of the cooling medium flowing from the first end to the second end, the temperature of the cooling medium may increase and efficiency of the cooling medium may decrease along the cooling medium absorbing more heat generated by the plurality of detecting cells of the detecting module (e.g., the detecting module 320 illustrated in FIG. 3A. When the cooling medium reaches the second end of the cooling plate 800 (e.g., a region C), the efficiency of the cooling medium may be lowest. The greater the length of the flow channel 807 in a region of the cooling plate is, the greater the area that the flow channel 807 in the region of the cooling plate 800 covers the plurality of detecting cells of the detecting module (e.g., the detecting module 320 illustrated in FIG. 3A) may be, and the greater the efficiency of the cooling medium for cooling the plurality of detecting cells of the detecting module (e.g., the detecting module 320 illustrated in FIG. 3A) may be. Thus a length of the flow channel 807 at the region C corresponding to the second end may be greater than other regions of the cooling plate, which may increase area that the flow channel 807 in the region C covers the plurality of detecting cells of the detecting module (e.g., the detecting module 320 illustrated in FIG. 3A), and improve efficiency of the cooling medium for cooling the plurality of detecting cells in the region C. Thus the temperature of the cooling plate 800 at different regions may be uniform, and a temperature gradient of the cooling plate 800 may be decreased to be smaller than a threshold, such as smaller than 1 degrees Celsius, or smaller than 0.8 degrees Celsius, or smaller than 0.6 degrees Celsius, etc.

In some embodiments, the cooling medium may further flow from the second end of the cooling plate 800 to the first end to absorb heat generated by the plurality of detecting cells again. As described above, the length of the flow channel 807 at a region A corresponding to the first end may be longer than the length of the flow channel 807 at the central region and/or the region C. In some embodiments, the flow channel 807 and the cooling plate 800 may be manufactured using an integrated molding technique which may increase a width of the flow channel 807, decrease flow resistance, and improve efficiency of the cooling medium for cooling the plurality of detecting cells.

Figure 8B:
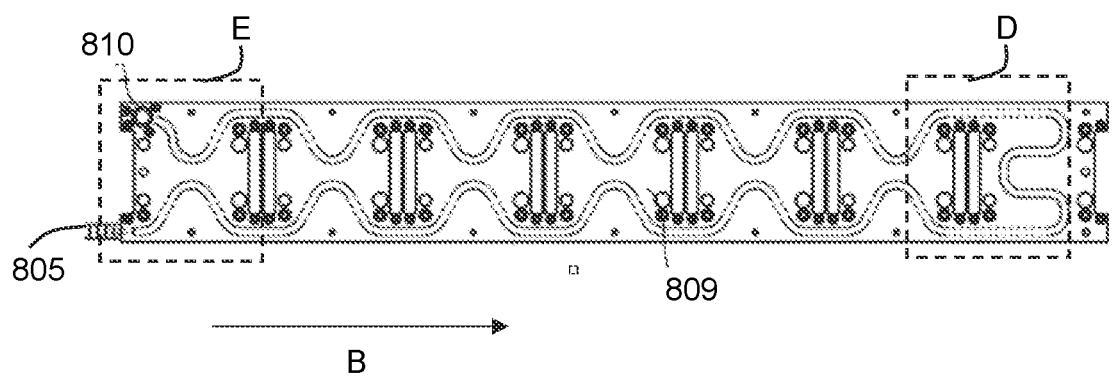

FIG. 8B is a schematic diagram illustrating an exemplary cooling plate 850 according to some embodiments of the present disclosure. As shown in FIG. 8B, the cooling plate 850 may include an outlet 805 and a flow channel 809.

The flow channel 809 may be configured to transfer, deliver, channel, or circulate a cooling medium to absorb heat produced by a component of a detector apparatus with a high energy consumption and/or uneven heating, such as one or more signal processing board of a detector apparatus (e.g., the detector apparatus 300 in FIG. 3, the detector apparatus 500 in FIG. 5, and/or the detector apparatus 600 in FIG. 6,) during an imaging procedure. The outlet 805 may be mounted at a first end of the cooling plate 850. In some embodiments, the flow channel 809 may be in flow communication with a refrigerator (not shown) via the outlet 805. For example, the used cooling medium after cooling the signal processing board may flow into the refrigerator via the outlet 805. In some embodiments, the flow channel 809 may be in flow communication with the refrigerator (not shown) via an inlet connected with a second end of the cooling plate 850. For example, the refrigerator may generate a cooling medium. The cooling medium may be driven by a pump to flow into the flow channel 809 via the inlet.

In some embodiments, the flow channel 809 may have a curved shape, a spiral shape, a straight line shape, a serpentine shape, a rectangular shape, or other eligible shape, or any combination thereof. The flow channel 807 and the flow channel 809 may have different shapes or a same shape. For example, the flow channel 807 may have a spiral shape arranged along the long axis direction (denoted by arrow B) of the cooling plate 850. The flow channel 809 may have a serpentine shape arranged along the long axis direction (denoted by arrow B) of the cooling plate 850. The serpentine shape of the flow channel 809 may decrease flow resistance of the cooling medium. In some embodiments, the flow channel 809 may be multiple layers. For example, the flow channel 809 may have a first layer from the first end to the second end arranged along the long axis direction (denoted by arrow B) of the cooling plate 850 and a second layer from the second end to the first end.

In some embodiments, a cooling medium may flow in the flow channel 809 from the first end of the cooling plate 850 corresponding to the first end to the second end of the cooling plate 850 to absorb heat generated by the plurality of detecting cells and then flow out of the cooling plate 850. In a process of the cooling medium flowing from the first end to the second end, the temperature of the cooling medium may increase the efficiency of the cooling medium may decrease along the cooling medium absorbing more heat generated by the signal processing board. When the cooling medium reaches the second end of the cooling plate 850 (e.g., a region D), efficiency of the cooling medium may be lowest. The greater the length of the flow channel 809 in a region of the cooling plate is, the greater the area that the flow channel 809 in the region of the cooling plate 850 covers the signal processing board may be, and the greater the efficiency of the cooling medium for cooling the signal processing board may be. Thus a length of the flow channel 809 at the region D corresponding to the second end may be greater than other regions of the cooling plate, which may increase area that the flow channel 809 in the region D covers the signal processing board, and improve efficiency of the cooling medium for cooling the plurality of detecting cells in the region D. Thus the temperature of the cooling plate 850 at different regions may be uniform, and a temperature gradient of the cooling plate 850 may be decreased to be smaller than a threshold, such as smaller than 1 degrees Celsius, or smaller than 0.8 degrees Celsius, or smaller than 0.6 degrees Celsius, etc.

In some embodiments, the cooling medium may further flow from the second end of the cooling plate 850 to the first end to absorb heat generated by the signal processing board again. As described above, the length of the flow channel 809 at a region E corresponding to the first end may be longer than the length of the flow channel 809 at the central region and/or the region E. In some embodiments, the flow channel 809 and the cooling plate 850 may be manufactured using an integrated molding technique which may increase a width of the flow channel 809, decrease flow resistance, and improve efficiency of the cooling medium for cooling the signal processing board.

In some embodiments, the heat produced by the signal processing board may be more than the heat produced by the plurality of detecting cells. And electronics units in the plurality of detecting cells may be more sensitive to the heat than electronics units of the signal processing board to the heat. Therefore, the length of the flow channel 807 may exceed the length of the flow channel 809.

In some embodiments, the cooling plate 800 and the cooling plate 850 may be integrated into one single cooling assembly. The cooling plate 800 and the cooling plate 850 may be in flow communication via the one or more connectors. The one or more connectors may have a first open 808 on the cooling plate 800 and a second open 810 on the cooling plate 850. The cooling medium may flow from the flow channel 807 to the flow channel 809 via the one or more connectors.

It should be noted that the above description of the fluid cooling assembly in FIGS. 8A and 8B is merely provided for the purposes of illustration, and not intended to limit the scope of the present disclosure. For persons having ordinary skills in the art, multiple variations or modifications may be made under the teachings of the present disclosure. For example, the cooling plate 800 and/or the cooling plate 850 may further include one or more components, and one or more components may be omitted or instead by other components. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an subject oriented programming language such as JAVA, SCALA, SMALLTALK, EIFFEL, JADE, EMERALD, C++, C#, VB. NET, PYTHON or the like, conventional procedural programming languages, such as the "C" programming language, Visual Basic, Fortran 2013, PERL, COBOL 2012, PHP, ABAP, dynamic programming languages such as PYTHON, RUBY, and GROOVY, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximately," or "substantially." For example, "about," "approximately," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A detector apparatus, comprising:
   a detecting module configured to detect radiation rays emitted from a subject and generate electrical signals in response to detection of radiation rays, wherein
   the detecting module includes a plurality of detecting cells arranged along an axial direction of a scanner including the detector apparatus, the axial direction being perpendicular to a circumferential direction of the scanner, each of the plurality of detecting cells includes a detecting unit and a first electronics unit, the detecting unit is configured to generate visible light signals in response to detection of the radiation rays, and the first electronics unit is configured to convert the visible light signals into electrical signals, at least one of the plurality of detecting cells is detachable from the detecting module;
   an electronics module configured to process the electrical signals generated by the detecting module; and
   a cooling assembly configured to cool the detecting module and the electronics module, the cooling assembly including a first layer and a second layer, wherein the first layer is thermally connected with the detecting module, and the second layer is thermally connected with the electronics module, each of the plurality of detecting cells is connected with a first cooling plate of the cooling assembly detachably via one or more connecting mechanisms.

2. The detector apparatus of claim 1, wherein the first layer is made of the first cooling plate, the second layer is made of a second cooling plate, and the first cooling plate is spatially separate from the second cooling plate.

3. The detector apparatus of claim 1, wherein the first layer and the second layer are part of the first cooling plate, the first layer and the second layer are thermally disconnected from each other, and the first cooling plate being mounted between the detecting module and the electronics module.

4. The detector apparatus of claim 1, wherein the cooling assembly further includes one or more thermally insulating layers mounted between the first layer and the second layer.

5. The detector apparatus of claim 1, wherein the first layer is in fluid communication with the second layer, the first layer includes a first flow channel and the second layer includes a second flow channel, the first flow channel and the second flow channel being configured to accommodate one or more cooling mediums.

6. The detector apparatus of claim 5, wherein the cooling assembly further includes one or more connectors, the first flow channel being in fluid communication with the second flow channel via the one or more connectors.

7. The detector apparatus of claim 6, wherein the cooling assembly further includes an inlet mounted on the first layer, and an outlet mounted on the second layer.

8. The detector apparatus of claim 5, wherein at least one of the first flow channel or the second flow channel has a curved shape, or the second flow channel has a serpentine shape.

9. The detector apparatus of claim 5, wherein a length of the first flow channel at a region corresponding to a second end of the first layer is greater than other regions of the first layer, a first end of the first layer being configured with an inlet.

10. The detector apparatus of claim 5, wherein a length of the second flow channel at a region corresponding to a second end of the second layer is greater than other regions of the second layer, a first end of the second layer being configured with an outlet.

11. The detector apparatus of claim 5, wherein a length of the first flow channel exceed a length of the second channel.

12. The detector apparatus of claim 1, wherein a temperature gradient of the detector apparatus is less than a threshold, wherein the threshold is 0.6 degrees Celsius.

13. The detector apparatus of claim 1, wherein a count of the plurality of detecting cells in the detector apparatus is adjustable.

14. The detector apparatus of claim 1, wherein the first layer is connected with the first electronics unit of each of at least a portion of the plurality of detecting cells.

15. The detector apparatus of claim 1, wherein the electronics module includes one or more second electronics units configured to process the electrical signals generated by at least one of the plurality of detecting cells, and each of the one or more second electronics units is associated with the at least one of the plurality of detecting cells.

16. The detector apparatus of claim 15, wherein each of the one or more second electronics units are connected with the second cooling plate of the cooling assembly detachably via one or more connecting mechanisms.

17. A detector apparatus of a scanner, comprising:
a detecting module configured to detect radiation rays emitted from a subject and generate electrical signals in response to detection of radiation rays; and
an electronics module configured to process the electrical signals generated by the detecting module, wherein
the detecting module includes a plurality of detecting cells arranged along an axial direction of the scanner, each of the plurality of detecting cells including a detecting unit and a first electronics unit, the detecting unit is configured to generate visible light signals in response to detection of the radiation rays, and the first electronics unit is configured to convert the visible light signals into electrical signals at least one of the plurality of detecting cells is detachable from the detector module and each of the plurality of detecting cells is connected with a first cooling plate detachably via one or more connecting mechanisms.

18. An imaging device, comprising:
a gantry comprising a detection region to accommodate a subject; and
a plurality of detector apparatuses arranged along a circumferential direction of the gantry, each of the plurality of detector apparatuses including a plurality of detecting cells and an electronics module arranged along an axial direction of the gantry that is perpendicular to the circumferential direction,
wherein at least one of the plurality of detecting cells are detachably mounted on the gantry and each of the plurality of detecting cells is connected with a first cooling plate detachably via one or more connecting mechanisms, each of the plurality of detecting cells includes a detecting unit and a first electronics unit, the detecting unit is configured to generate visible light signals in response to detection of radiation rays, and the first electronics unit is configured to convert the visible light signals into electrical signals, and the electronics module configured to process the electrical signals generated by the plurality of detecting cells.

* * * * *